United States Patent [19]
Rotteveel et al.

[11] Patent Number: 5,299,578
[45] Date of Patent: Apr. 5, 1994

[54] ENDOSCOPIC PROBE

[75] Inventors: Bart J. Rotteveel, Delft, Netherlands; Pieter D. Brommersma, Hamburg, Fed. Rep. of Germany

[73] Assignee: B.V. Optische Industrie "De Oude Delft", Delft, Netherlands

[21] Appl. No.: 969,209

[22] PCT Filed: Jul. 31, 1991

[86] PCT No.: PCT/NL91/00143
§ 371 Date: Feb. 22, 1993
§ 102(e) Date: Feb. 22, 1993

[87] PCT Pub. No.: WO92/02180
PCT Pub. Date: Feb. 20, 1992

[30] Foreign Application Priority Data
Aug. 2, 1990 [NL] Netherlands .......................... 9001755

[51] Int. Cl.[5] .................................................. A61B 8/12
[52] U.S. Cl. ................................ 128/662.06; 128/663.01; 128/660.08
[58] Field of Search .................. 128/662.06, 663.01, 128/660.09, 660.08

[56] References Cited
U.S. PATENT DOCUMENTS

| | | | |
|---|---|---|---|
| 4,957,112 | 9/1990 | Yokoi et al. | 128/662.06 |
| 5,195,519 | 3/1993 | Angelsen | 128/662.06 |

Primary Examiner—William E. Kamm
Assistant Examiner—George Manuel
Attorney, Agent, or Firm—Louis E. Marn

[57] ABSTRACT

An endoscopic probe suitable for use as a TEE-probe, comprising a flexible tube having at one end a probe head which is provided with a phased array ultrasonic transducer with a number of elongated transducer elements which can be individually electrically controlled by cables connected to the individual elements and extending through a flexible tube in which the transducer is mounted in a cylindrical transducer housing, which is in a cavity in the probe head and is rotatable about a longitudinal axis extending at right angles to the longitudinal axis of the probe head, by means of a drive means interacting with the transducer housing while the elongated transducer elements are connected by flexible conductors to the cables extending through the flexible tube and in which a convex acoustic lens is mounted on the transducer and the peripheral edge of the lens interacts in a sealing manner with the edge of the cavity in the probe head and can rotate together with the transducer relative to the probe head.

19 Claims, 5 Drawing Sheets

ENDOSCOPIC PROBE

The invention relates to an endoscopic probe, in particular suitable for use as a TEE probe, comprising a flexible tube having at one end a probe head which is provided with ultrasonic transducer means of the phased array type with a transducer made up of a number of elongated transducer elements, which elements can be individually electrically controlled by means of cables connected to the individual elements and extending through the flexible tube, the transducer being mounted in an essentially cylindrical transducer housing which is placed in a cavity with an aperture in the probe head and is rotatable about a longitudinal axis extending at right angles to the longitudinal axis of the probe head by means of drive means interacting with the transducer housing while the elongated transducer elements are connected by means of flexible conductors to the cables extending through the flexible tube.

An endoscopic probe is known from the article "An endoscopic micromanipulator for multiplanar transesophageal imaging" by Roy W Martin et. al. in Ultrasound in Med & Biol., Vol 12, No 12, pp. 965-975, 1986. The known probe has a probe head with a slightly flattened part containing an essentially flat transducer made up of a number of individual adjacent elongated elements of piezoelectric material which can be excited individually, and which together form a phased array. By exciting the strip-type elements in a suitable sequence, it is possible to obtain a beam which scans the environment to be examined and produces reflections in a plane lying at right angles to the elongated elements, as described in greater detail by J. C. Somer in "Echocardiography", N. Bom, published by Martinus Nijhof in The Hague, 1977. Rotating the flexible tube and thus the probe head, about the longitudinal axis means that the environment around the probe head can be scanned by an ultrasonic beam. Pulling cables also extend through the flexible tube, by means of which said head can be pulled forwards or backwards.

In the medical world there is a need for an endoscopic probe with which more information can be obtained. In the past it was proposed that a biplane TEE probe should be used for this purpose. Such a probe head has two transducer arrays lying one after the other in the lengthwise direction of the flexible tube and the head, each again composed of adjacent elongated elements. The elements of one transducer extend at right angles relative to the elements of the other transducer. With this head it is therefore possible to obtain two scanning beams which can carry out a scanning movement in directions extending at right angles to each other.

A disadvantage of this known probe is that the scanning beams originate in two different points. Another disadvantage is that the rigid head is relatively long, which can lead to problems in practical use. Two separate transducer arrays with the same definition per array also require twice the number of control cables, which all have to be conveyed through the flexible tube. However, the flexible tube has little or no pace for these.

In order to eliminate these problems, it was proposed in U.S. Pat. No. 4,543,960 that the transducer array should be fitted in the probe head so that it is rotatable about an axis extending at right angles to the plane of the array. For this, a transducer housing, bearing the transducer array and rotatable about a pin provided on the side of the transducer housing facing away from the array, is fitted in a cavity in the probe head. The elements of the transducer array are connected by means of conductors formed on two flexible printed circuit boards to the different cores of one or more electrical cables extending through the flexible tube.

The flexible printed circuit boards lie coiled around the transducer housing.

It is not indicated in U.S. Pat. No. 4,543,960 whether, and if so in what way, the cavity in which the transducer housing with the transducer is situated is sealed off relative to the environment. A good seal with as few seams and crevices as possible is, however, necessary from the point of view of hygiene if the probe is intended for repeated use.

The object of the invention is therefore to provide an endoscopic probe which meets the abovementioned requirement, and more generally to provide an endoscopic probe which is suitable for repeated use on different patients, and by which the human body can he examined internally by echography in the optimum manner.

For this, according to the invention an endoscopic probe of the above-described type is characterised in that a convex acoustic lens is fixed on the transducer said lens being provided in said aperture, and the peripheral edge of the lens interacts in a sealing manner with the edge of the aperture in the probe head such that the cavity is sealed at the level of the aperture by the lens and that the lens is rotatable together with the transducer relative to the probe head.

The invention will be described in greater detail below with reference to the appended drawing of a number of examplary embodiments.

Figure 1:
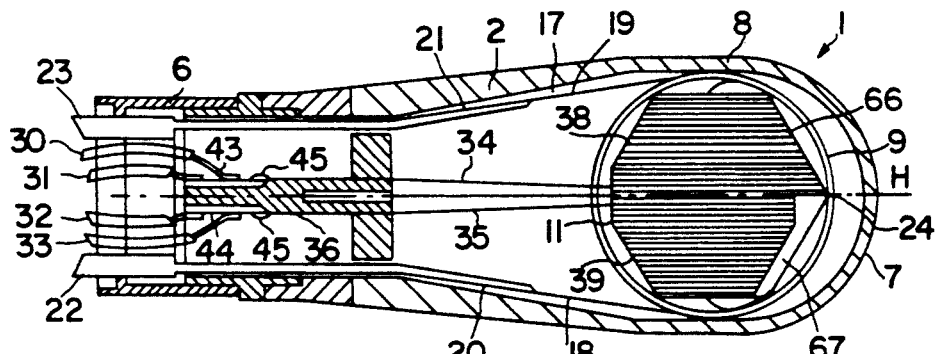
FIG. 1 shows schematically a cut-away top view of an examplary embodiment of a probe head of a TEE probe according to the invention.
Figure 2:
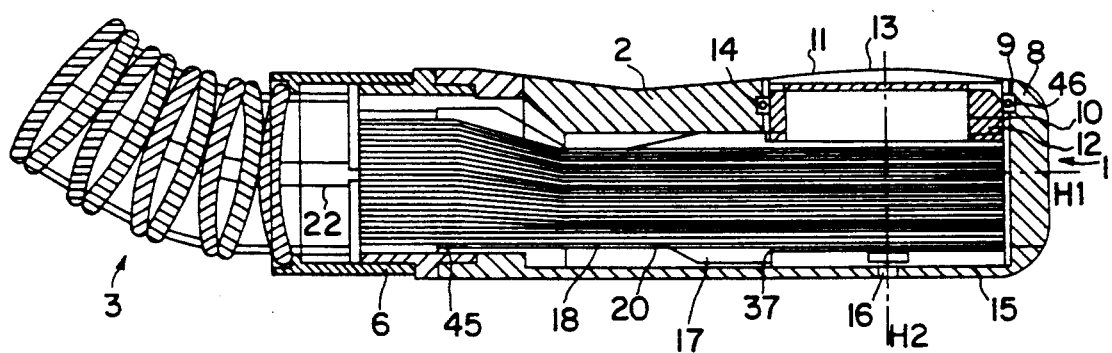
FIG. 2 shows schematically a cut-away side view of the probe head of FIG. 1.
Figure 3:
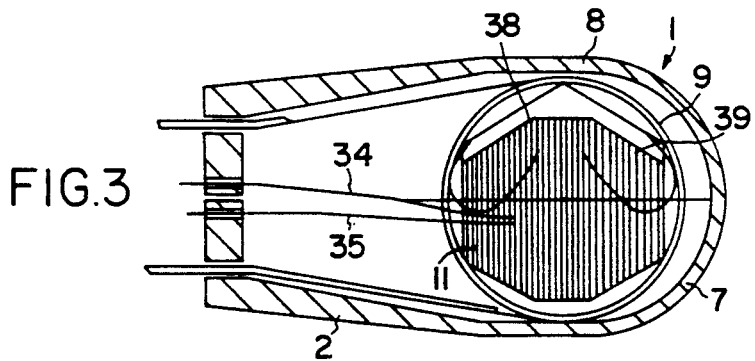
FIG. 3 shows schematically a top view of the probe head of FIG. 1, in a different working position.

FIGS. 1 to 3 show a TEE probe as an examplary embodiment of the invention. A TEE (trans esophageal echocardiography) probe is a device which can be used to examine the heart, or other parts of the body in the region of the oesophagus, by ultrasonic radiation from the oesophagus through the oesophagus wall. The device shown comprises a probe head 1 with a housing 2, which connects to a flexible end part 3 of a flexible tube which is not shown. Using Bowden cables 4, 5 extending through the flexible tube, the probe head can be bent forwards (as shown in FIG. 2) or backwards. This movement is made possible by the end part 3. If desired, similar Bowden cables which permit a sideways swing of the probe head can be present.

The housing 2 connects by means of a connecting piece 6 with round cross-section to the end part 3 of the flexible tube, but itself has an essentially rectangular cross-section with rounded edges which widens out slightly to a holder 8 which is shut off at the free end by a semi-circular wall 7, and in which an ultrasonic transducer of the phased array type is placed. The holder 8 is provided with a circular aperture 9 in an essentially flat top wall. Situated in and behind the aperture is the transducer which, as can be seen in FIG. 2, comprises an essentially flat transducer 11 lying on a backing layer 10. The transducer 11 is made up of a number of adjacent, but separate strip-type transducer elements which can be, for example, piezoelectric elements, and which in the situation shown in FIG. 1 extend parallel to the longitudinal axis H of the probe head. The backing layer absorbs ultrasonic vibrations which are radiated towards the interior of the probe head and which, if not absorbed, would lead to disturbing reflections. The backing layer 10 is confined inside an electrically insulating frame 12 which can be made of, for example, a suitable plastic.

Above the array 11 is an acoustic lens 13, which will be described in greater detail below. In a suitable manner phasedly exciting the individual strip-type transducer elements makes it possible to obtain an ultrasonic beam which can scan an area the shape of a sector of a circle in a plane at right angles to the strip-type elements. This technique, which is known per se, can therefore be used to scan the environment of the probe head with a swinging beam, but the swing can take place in only one plane.

The lens 13, the transducer 11, the frame 12 and the backing layer 10 are placed in a transducer housing 14 which is an essentially cylindrical shape. The transducer housing is sealed at the level of the aperture 9 by the lens 13, and in the example shown also has a bottom 15 which is supported on a pin 16 fitted in a bore in the wall of the housing opposite the aperture 9. The central axis of the pin coincides with the central axis H2 of the transducer housing, and the centre point of the circular opening lies on said central axis H2, so that the transducer housing is rotatable about the pin.

In the examplary embodiment shown the transducer housing is rotatable from the rest position shown in FIG. 1 both clockwise and anticlockwise through approximately 90 degrees. FIG. 3 shows the probe head with a transducer 11 rotated through 90 degrees. The total rotation range is therefore 180 degrees, which means that a spatial area the shape of the sector of a sphere can be scanned completely with one and the same disc-type transducer made up of strips, without changing the position of the probe head itself.

In order to make the transducer housing 14 rotate in this example, a belt 17 is passed around the transducer housing, the two free ends 18, 19 of which belt are connected to pulling cables 20, 21. The pulling cables are again in the form of Bowden cables, the outer cables of which are shown at 22, 23. The belt 17 can be a spring steel belt which 18 connected at one point to the transducer housing 14, for example by a single spot weld. The connection in the rest position is on or near the longitudinal axis H1 of the probe head, as shown at 24 in FIGS. 1 and 4.

Figure 4:
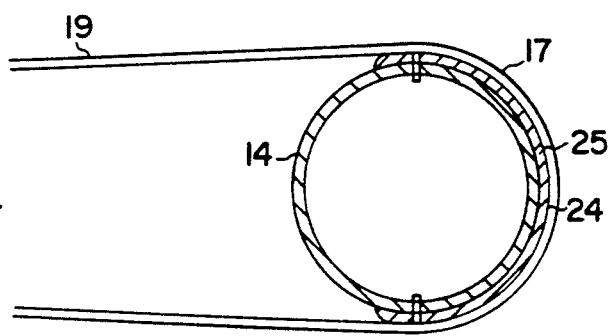
FIG. 4 shows detail of the probe of FIG. 1 and FIG. 2.

All this is shown again in FIG. 4. An interposed metal strip is indicated by 25 and is connected in a suitable manner to the transducer housing. This prevents the pulling belt from slipping over the transducer housing.

For the electrical connection between the transducer elements and the electrical cables passed through the flexible tube, use is made of a flexible printed circuit board on which conductor tracks, connected at one side to the individual transducer elements and at the other side to the cores of the electric cables, are provided.

A number of cables are indicated by 30 to 33 in FIG. 1. The flexible printed circuit board is indicated by 34, 35. The flexible printed circuit board extends from a supporting plate 36 situated in the part of the probe head 1 connecting to the flexible tube and reaches into the transducer housing 14. For this purpose, the transducer housing is provided with a recess 37 extending through approximately 180 degrees along the periphery and being the height of the width of the flexible printed circuit board. Fitted in the transducer housing 14 under the backing layer are two pins 38, 39 which are fixed on the bottom 15 and/or in the backing layer 10. A strip of the flexible printed circuit board is passed around each of the pins 38, 39. Each strip extends in a loop under the backing layer towards connecting electrodes fitted on one end of the strip-type transducer elements. The flexible printed circuit boards thus do not take up any space around the transducer housing.

In the examplary embodiment shown, the connecting electrodes for all strip-type elements are on the front side of the probe head. It is, however, also possible, for example. to fit the electrodes for the even-numbered elements on the front side and the electrodes for the odd-numbered elements on the opposite side of the transducer.

The pins 38, 39 are preferably placed in such a way that the flexible printed circuit boards extend essentially through the axis of rotation H2 of the transducer housing not only in the rest position shown in FIG. 1, but also on rotation of the transducer housing. Rotation of the transducer housing 14 therefore does not lead to a change in the space required for the flexible printed circuit boards.

The parts of the flexible printed circuit boards extending outside the transducer housing change position only to a very small extent during rotation of the transducer housing, as can be seen from a comparison of FIGS. 1 and 3.

The pins 38, 39 can be positioned as shown on both sides of the longitudinal axis H just past the centre line extending at right angles to the longitudinal axis.

The supporting partition 36 in this example bears on both sides printed circuit boards 43, 44 with conductor tracks to which the ends of the cables 30 to 33 are connected. The connecting point between the conductors of the printed circuit boards 43, 44 and the conductors of the flexible printed circuit board is indicated at 45.

Figure 5:
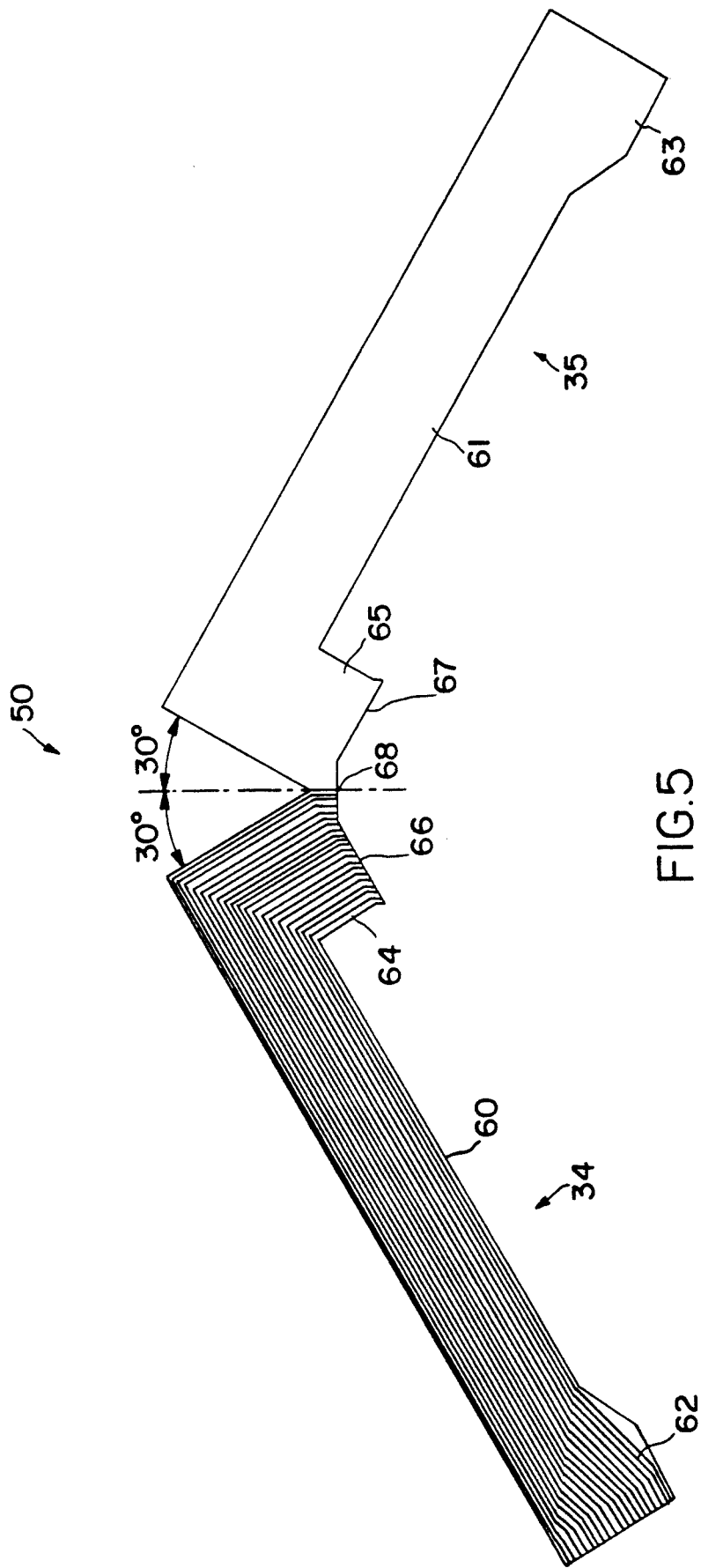
FIG. 5 shows an example of a special printed circuit board which can be used in a probe according to the invention.

FIG. 5 shows schematically a flat blank of a flexible printed circuit board 60 which can be used in the device described. The printed circuit board shown has two wing strips 34, 35 which together form an approximately V-shaped flat blank. Each wing 34, 35 has an elongated part 60, 61 which has a first end 62, 63 for connection to the printed circuit boards 43, 44.

Each wing also has a short transverse part 64, 65 which in the fitted state rests against the frame 12 at the front side (in FIG. 1 or FIG. 2). The transverse parts each have an end strip 66, 67. The end strips of the two transverse parts are connected to each other at 68 and thus form the connection between two wing strips. The end strips in the fitted state are folded over approximately at right angles and at the bottom side lie against the connecting electrodes of the transducer elements. The connecting electrodes can be, for example, gold-electrodes, and the connection can be made with conducting adhesive.

It is pointed out that the width of the elongated parts of the wing strips: of the flexible printed-circuit board described together with the thickness resulted for the backing layer largely determines the minimum height of the probe head. According to a further development of the idea of the invention, the elongated parts 60, 62 in the fitted state are folded double about a fold line extending in the lengthwise direction.

Figure 6:
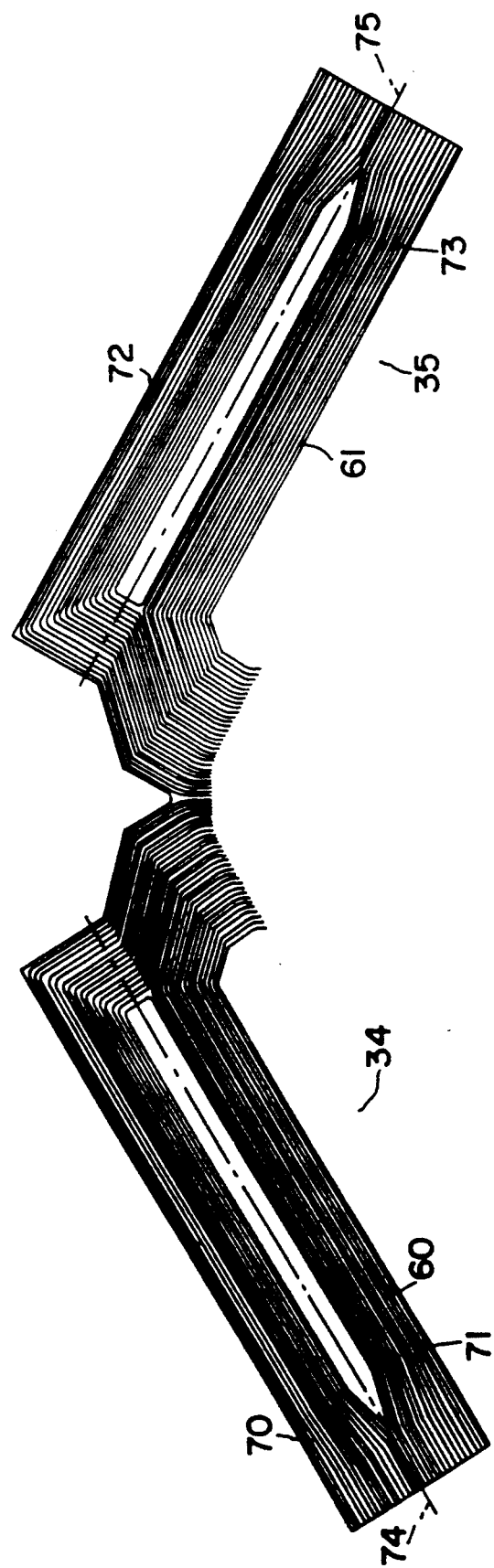
FIG. 6 shows a modification of the flexible printed circuit board of FIG. 5.

An example of a flat blank for a flexible printed circuit board used for this purpose is shown in FIG. 6. The conductor tracks extending in the lengthwise direction of the elongated parts 60, 61 of the wing strips 34, 35 of the flexible printed circuit board are in each case divided into two groups 70, 71 and 72, 73 lying on both sides of a fold line 74, 75. The height required for the flexible printed circuit board is thereby greatly reduced.

When a flexible printed circuit board with double-folded elongated parts of the wing strips is used, if one or more printed circuit boards 43, 44 are again used as the connecting elements between the cables 30 to 33 and the flexible printed circuit board, the printed circuit board 43 and/or 44 can be provided with conductors on both sides. In this case each side of a printed circuit board 43 or 44 can, for example, correspond to one of the parts 70 to 73.

In principle, two (or more) individual flexible printed circuit boards could also be used. The use of a single printed circuit board gives the advantage that the position of the tracks, in particular in the end strips, is determined accurately. With the correct selection of the centre-to-centre distance of the tracks these can also be placed accurately in line with the gold electrodes of the transducer elements and after correct positioning of a printed circuit board shifting of any second printed circuit board cannot take place.

Figure 7:
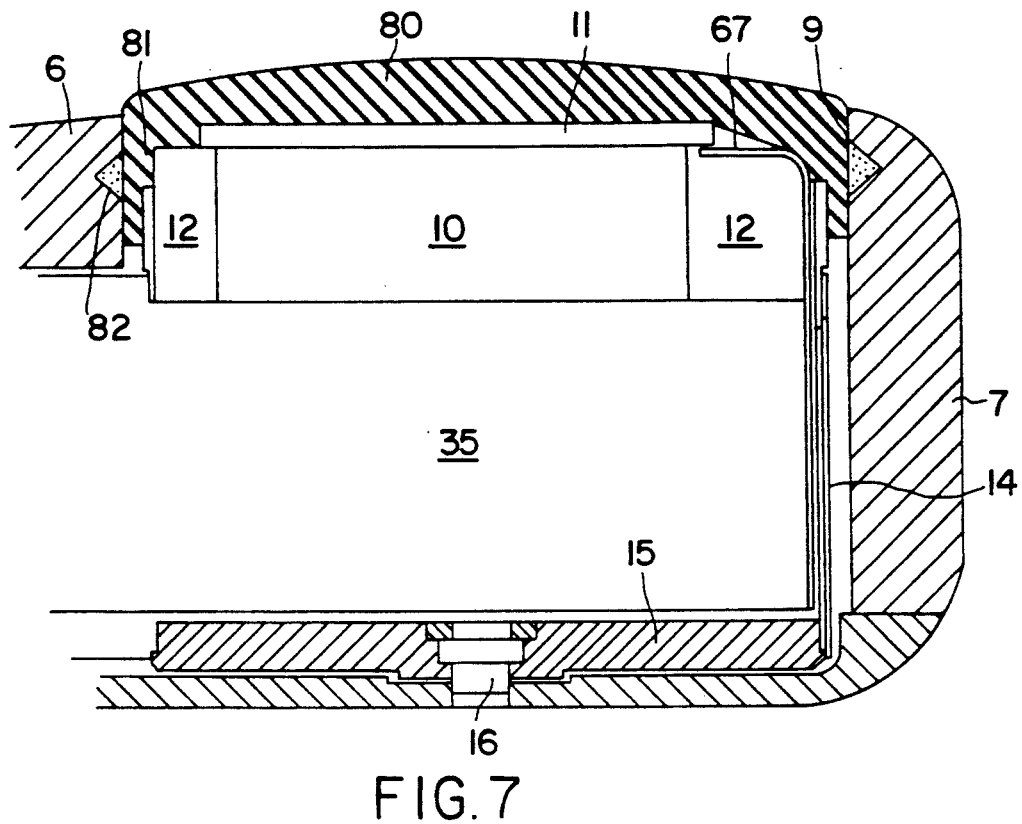
FIG. 7 shows schematically a first example of an embodiment of a seal between a rotatable acoustic lens and the remainder of the probe head.

FIG. 7 shows schematically in longitudinal section a first example of an embodiment of an acoustic lens 80 serving as a sealing cap for the cavity in the probe head. The lens 80 is a convex lens which can be made of, for example, silicone rubber of the RTV-J type. The lens shown has a convex central part which is fixed on the rotatable transducer and a cylindrical downgoing outer wall 81 which lies in a close fit in the aperture 9 in the probe head. A sealing means is provided between the wall of the aperture shown comprises a peripheral groove 82 filled with a friction-reducing agent such as grease. The groove in this example is formed in the wall of the aperture 9, but could also be fitted in the outer wall of the lens, as shown at 83 in FIG. 8.

Figure 8:
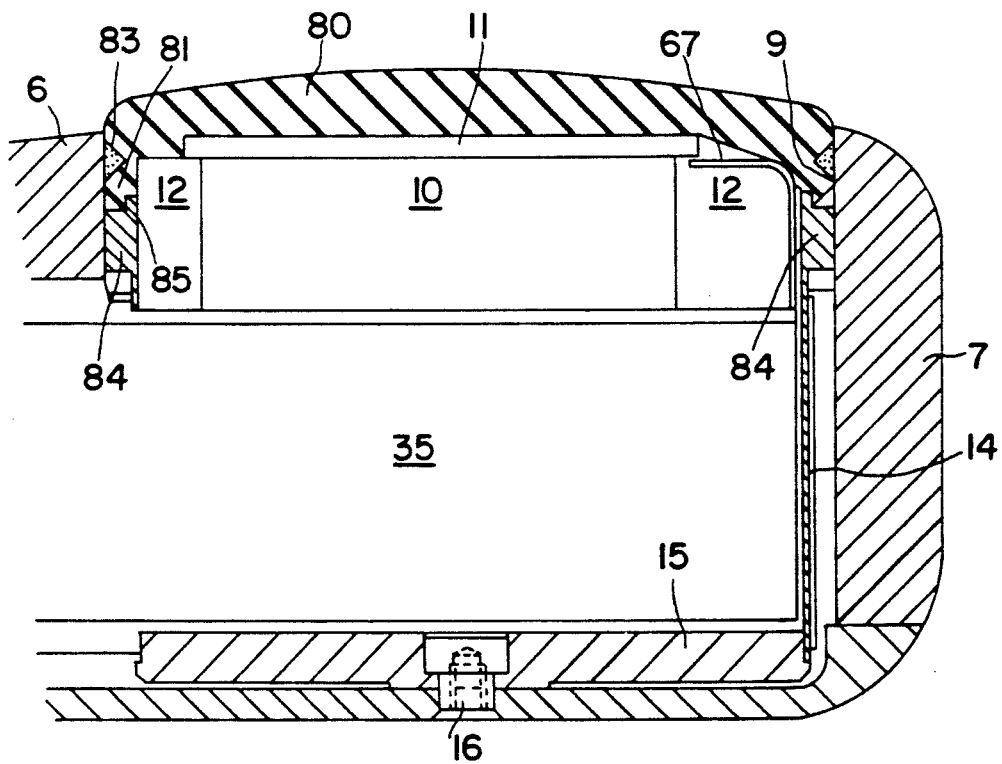
FIG. 8 shows schematically a variant of FIG. 7.

In the example of FIG. 8 the housing 14 is also provided with an annular peripheral edge 84 which lies in a close fit, but rotatably against the wall of the aperture 9 and promotes an accurate support and positioning of the lens in the radial direction. The cylindrical wall 81 of the lens connects in the axial direction, and through use of a shoulder 85 also in the radial direction, in a positive fit to the peripheral edge 84 of the housing 14. A suitable screening foil, for example of aluminium capton (polyimide) can be provided between the transducer 11 and the convex lens.

Figure 9:
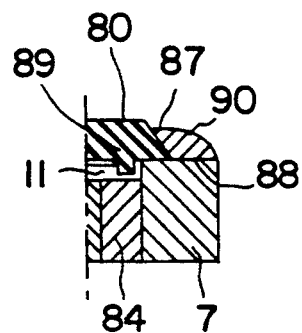
FIGS. 9 to 11 show schematically a number of other examplary embodiments of a lens which is rotatable relative to the remainder of the probe head.

FIG. 9 shows another example of an embodiment in which a convex lens 80, lying with a radial shoulder 87 on a flat top edge 88 of the probe head surrounding the aperture 9, is again used. The lens also has a cylindrical edge 89 which falls into the aperture 9. A ring 90 is placed over the radial shoulder 87, said ring being firmly fixed to the flat top edge 88 of the probe head and having an undercut filled with grease which accommodates the radial shoulder. The outer edge of the ring 90 is rounded, as indicated at 91. The ring 90 can be glued on the flat top edge. The housing 14 again has a part 84 which lies radially against the wall of the cavity in the probe head.

Figure 10:
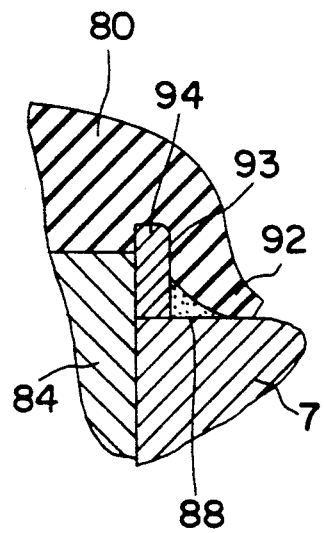
Figure 11:
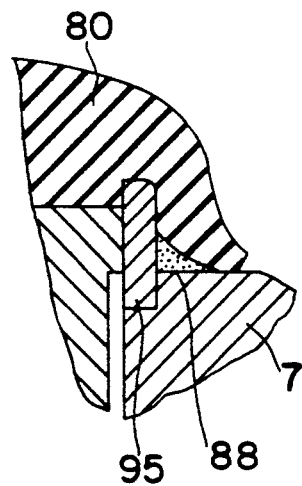

In the examplary embodiment shown in FIG. 10, the convex lens 80 is provided with a peripheral lip 92. The lip rests slightly resiliently against the top edge of the probe head. An axial groove 93 is fitted in the bottom side of the lens, radially slightly inwards from the lip. A ring 94 of hard material, for example glass ceramic material such as MACOR, is fixed in the groove 93, for example by means of adhesive The ring can turn with little friction over the material of the probe head. In FIG. 10 the ring lies on the top edge 88 of the probe head, but the ring can also extend in a groove along the edge of the cavity, as shown in FIG. 11 at 95.

In the example shown, the ring is also glued to the adjacent part of the housing 14.

In the cavity below the lip of the concave lens there is again grease, which has both a lubricating and a sealing effect.

It is pointed out that, after the above, various modifications are obvious for the expert. For example, instead of the belt 17 a circular pulling cable, provided with a nipple falling into a cavity of the transducer housing, can be used.

As an alternative, the belt 17 could be replaced by yet another transmission mechanism such as a toothed rack which can be shifted by a pulling cable in the lengthwise direction, and which engages on a toothed wheel coupled directly or indirectly to the transducer housing In that case it would be possible to make do with one pulling cable. Springs which press the transducer housing back to a predetermined rest position can also be used.

Instead of a single flexible printed circuit board, as already stated, two or more flexible printed circuit boards or one or more bunches of wires connected between the connectors 40, 41 and to the cables 30 to 33 could be used.

The belt 17 can also be made narrower and is preferably slightly recessed in a groove in the transducer housing.

The transducer, which in the example shown is essentially flat and hexagonal, can also be, for example, round or rectangular and slightly convex or even concave.

It is also pointed out that the probe described can also in principle be used for examination through body cavities other than the oesophagus.

These and similar modifications are considered to fall within the scope of the invention.

We claim:

1. An endoscopic probe particularly suitable for use as a TEE probe, comprising a flexible tube having at one end a probe heat comprising an ultrasonic transducer means of the phased array type including a number of elongated transducer elements individually electrically controlled by cables connected to said individual controlled transducer elements extending through said flexible tube, said ultrasonic transducer means being mounted in an essentially cylindrical transducer housing placed in a cavity in said probe head and rotatable about a longitudinal axis of said probe head by drive means interacting with said transducer housing said elongated transducer elements being connected by flexible conductors to said cables extending through said flexible tube, a convex acoustic lens is fixed on said ultrasonic transducer means with a peripheral edge of said lens interacting in a sealing manner with an edge of said cavity in said probe head, said convex acoustic lens rotatable together with said ultrasonic transducer means relative to said probe head.

2. The endoscopic probe according to claim 1 wherein said acoustic convex lens has a cylindrical peripheral portion closely fitted but rotatably within said cavity, and wherein a grease-filled groove is provided in an outer wall of said cylindrical peripheral portion of said acoustic convex lens.

3. The endoscopic probe according to claim 1 wherein said acoustic convex lens has a cylindrical peripheral portion closely fitted, but rotatably within said cavity, and wherein a grease-filled groove is provided in an inner wall of said cavity at a level of said cylindrical peripheral portion.

4. The endoscopic probe according to claim 2 or 3 wherein said cylindrical peripheral portion connects axially to a top edge of said transducer housing.

5. The endoscopic probe according to claim 4 wherein said top edge of said transducer housing and said cylindrical peripheral portion have complementary connector shoulders.

6. The endoscopic probe according to claim 1 wherein said acoustic convex lens comprises along an outer periphery thereof a radial shoulder having a flat bottom face lying on a flat part of a top edge of said probe head enclosing said cavity, and wherein said radial shoulder is confined under a ring firmly fixed on said top edge of said probe head, said ring having an inside undercut falling over said shoulder and filled with grease.

7. The endoscopic probe according to claim 6 wherein said acoustic convex lens has an axial shoulder just falling inside said cavity.

8. The endoscopic probe according to claim 1 wherein said acoustic convex lens comprises at a bottom side near said cylindrical peripheral edge an axial groove in which a ring is fixed in a closely fitting manner, said ring interacting in a sealing manner with said edge of said cavity.

9. The endoscopic probe according to claim 8 wherein said acoustic convex lens has a peripheral lip lying radially outside said ring and rests slightly resiliently against said top edge of said probe head a chamber formed between said cylindrical peripheral edge, said ring and said top edge of said probe head being fitted with grease.

10. The endoscopic probe according to claim 8 or 9 wherein said ring is of a glass ceramic material.

11. The endoscopic probe according to claims 8 or 9 wherein said ring is partly disposed into a recess in said top edge of said probe head.

12. The endoscopic probe according to claims 1, 2 or 3 wherein said flexible conductors are tracks formed on a flexible printed circuit board extending through an aperture into said transducer housing positioned in a loop shape in said transducer housing towards said connecting electrodes of transducer elements.

13. The endoscopic probe according to claim 12 wherein said flexible printed circuit board extends with a part lying between said cables and said loop shape proximate said longitudinal axis of said transducer housing and wherein said aperture in said transducer housing forms an angle or arc of essentially 180°.

14. The endoscopic probe according to claim 12 or 13, wherein said flexible printed circuit board is passed round a pin fitted in said transducer housing.

15. The endoscopic probe according to claim 14 wherein said flexible printed circuit board is attached between two pins fitted in said transducer housing, said pin extending essentially parallel to said longitudinal axis of said transducer housing and, when viewed from a part of said flexible printed circuit board connected to said cables, are fitted just past said longitudinal axis of said transducer, and in a rest position of said transducer housing are situated on both sides of said longitudinal axis of said probe head.

16. The endoscopic probe according to claim 12 or 13 wherein said transducer housing has a backing layer disposed inside an insulating frame on which said transducer means is positioned.

17. The endoscopic probe according to claim 16 wherein said flexible printed circuit board is positioned under said backing layer in said transducer housing.

18. The endoscopic probe according to claims 12 or 13 wherein a flexible printed circuit board in opened-out form is approximately V-shaped with two wing strips, each said wing strip having an elongated part and a short transverse part and connected to each other at a point of transverse sections, each transverse section having an end strip on which said conductors terminate and where said conductors are connected to said individual transducer elements.

19. The endoscopic probe according to claim 18 wherein elongated sections of said wing strips have at least two groups of conductor tacks lying on both sides of a fold line extending in a lengthwise direction of said wing strips, and wherein each wing strip is folded double along said fold line.

* * * * *